United States Patent
Azizian et al.

(10) Patent No.: US 12,376,749 B2
(45) Date of Patent: Aug. 5, 2025

(54) SYSTEM AND METHOD FOR SPECULAR REFLECTION DETECTION AND REDUCTION

(71) Applicant: INTUITIVE SURGICAL OPERATIONS, INC., Sunnyvale, CA (US)

(72) Inventors: Mahdi Azizian, San Jose, CA (US); Jonathan Sorger, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/435,905

(22) Filed: Feb. 7, 2024

(65) Prior Publication Data

US 2024/0298900 A1     Sep. 12, 2024

Related U.S. Application Data

(60) Division of application No. 16/562,121, filed on Sep. 5, 2019, now Pat. No. 11,937,899, which is a (Continued)

(51) Int. Cl.
    *A61B 5/00*        (2006.01)
(52) U.S. Cl.
    CPC .......... *A61B 5/0071* (2013.01); *A61B 5/0033* (2013.01); *A61B 5/7405* (2013.01); *A61B 5/742* (2013.01); *A61B 2576/00* (2013.01)
(58) Field of Classification Search
    CPC ... A61B 5/0071; A61B 5/0033; A61B 5/7405; A61B 5/742; A61B 2576/00
    See application file for complete search history.

(56) References Cited

U.S. PATENT DOCUMENTS

| 6,055,322 A | 4/2000 | Salganicoff et al. |
| 6,818,903 B2 | 11/2004 | Schomacker et al. |

(Continued)

FOREIGN PATENT DOCUMENTS

| CN | 1798968 A | 7/2006 |
| CN | 1949833 A | 4/2007 |

(Continued)

OTHER PUBLICATIONS

Bakker G., "Color Coding and the RGB Color Space," RGB explained (published online on Apr. 6, 2015), Retrieved from URL:https://geraldbakker.nl/psnumbers/rgb-explained.html, 07 pages (Year: 2015).

(Continued)

*Primary Examiner* — Chao Sheng
(74) *Attorney, Agent, or Firm* — Haynes & Boone. LLP

(57) ABSTRACT

A system and method of specular reflection detection and reduction includes a processing unit including one or more processors and an imaging unit coupled to the processing unit. The imaging unit includes one or more first illuminators for providing illumination of a region of interest, one or more first detectors for detecting reflections of the illumination, one or more second illuminators for triggering fluorescing of one or more fluorescent materials in the region of interest, and one or more second detectors for detecting the fluorescing of the fluorescent materials. The processing unit is configured to receive a first image from the first detectors, determine one or more regions of high specular reflection in the first image, mask out the regions of high specular reflection in the first image, and generate a composite image based on the masked first image and the detected fluorescence. The first image includes the detected reflections.

20 Claims, 4 Drawing Sheets

Related U.S. Application Data continuation of application No. 15/122,121, filed as application No. PCT/US2015/017950 on Feb. 27, 2015, now Pat. No. 10,426,347.

(60) Provisional application No. 61/945,660, filed on Feb. 27, 2014.

(56) References Cited

U.S. PATENT DOCUMENTS

| | | |
|---|---|---|
| 7,630,002 B2 | 12/2009 | Jenkins |
| 8,212,857 B2 | 7/2012 | Keam |
| 8,224,045 B2 | 7/2012 | Burns et al. |
| 8,320,702 B2 | 11/2012 | Ford |
| 8,324,602 B2 | 12/2012 | Wiese et al. |
| 10,426,347 B2 | 10/2019 | Azizian et al. |
| 11,937,899 B2 | 3/2024 | Azizian et al. |
| 2002/0103439 A1 | 8/2002 | Zeng et al. |
| 2002/0138008 A1 | 9/2002 | Tsujita et al. |
| 2002/0177777 A1 | 11/2002 | Nordstrom et al. |
| 2004/0184648 A1 | 9/2004 | Zhang et al. |
| 2006/0043194 A1 | 3/2006 | Barkan et al. |
| 2007/0081168 A1 | 4/2007 | Johnston |
| 2007/0181692 A1 | 8/2007 | Barkan et al. |
| 2008/0062429 A1 | 3/2008 | Liang et al. |
| 2008/0170764 A1* | 7/2008 | Burns .................. A61B 5/0088 382/128 |
| 2010/0103250 A1 | 4/2010 | Ishihara et al. |
| 2011/0116710 A1 | 5/2011 | Garg et al. |
| 2011/0304705 A1 | 12/2011 | Kantor et al. |
| 2012/0242861 A1 | 9/2012 | Zimmer |
| 2013/0092838 A1 | 4/2013 | Weber et al. |
| 2014/0098092 A1 | 4/2014 | Isokawa et al. |
| 2014/0267623 A1* | 9/2014 | Bridges .................. G06T 7/70 348/46 |
| 2015/0010878 A1 | 1/2015 | Seibel et al. |
| 2019/0387974 A1 | 12/2019 | Azizian et al. |

FOREIGN PATENT DOCUMENTS

| | | |
|---|---|---|
| CN | 101031930 A | 9/2007 |
| CN | 101588750 A | 11/2009 |
| CN | 101686820 A | 3/2010 |
| CN | 102301694 A | 12/2011 |
| EP | 2339534 A1 | 6/2011 |
| JP | H07250812 A | 10/1995 |
| JP | 2001224549 A | 8/2001 |
| JP | 2001258820 A | 9/2001 |
| JP | 2004220438 A | 8/2004 |
| JP | 2005106507 A | 4/2005 |
| JP | 2008183349 A | 8/2008 |
| JP | 2008204188 A | 9/2008 |
| JP | 2008233107 A | 10/2008 |
| JP | 2008271386 A | 11/2008 |
| JP | 2009128345 A | 6/2009 |
| JP | 2010509993 A | 4/2010 |
| JP | 2010516332 A | 5/2010 |
| JP | 2011522400 A | 7/2011 |
| JP | 2012048579 A | 3/2012 |
| JP | 2013020475 A | 1/2013 |
| JP | 2013150122 A | 8/2013 |
| JP | 2013188244 A | 9/2013 |
| JP | 2013258627 A | 12/2013 |
| WO | WO-2011061940 A1 | 5/2011 |
| WO | WO-2013109978 A1 | 7/2013 |

OTHER PUBLICATIONS

Extended European Search Report for Application No. EP20201765.3 mailed on Feb. 22, 2021, 07 pages.

Extended European Search Report for Application No. 15755954.3, mailed on Sep. 14, 2017, 7 pages (ISRG05710/EP).

International Preliminary Report on Patentability for Application No. PCT/US15/17950, mailed on Sep. 9, 2016, 13 pages (ISRG05710/PCT).

International Search Report and Written Opinion for Application No. PCT/US15/17950, mailed on May 29, 2015, 16 pages (ISRG05710/PCT).

Office Action for Chinese Application No. CN202010452939.7, mailed Aug. 1, 2023, 20 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for Chinese Application No. CN202010452939.7, mailed Jun. 5, 2024, 15 pages.

* cited by examiner

SYSTEM AND METHOD FOR SPECULAR REFLECTION DETECTION AND REDUCTION

RELATED APPLICATIONS

This application is a divisional of U.S. patent application Ser. No. 16/562,121, filed Sep. 5, 2019, which is a continuation of U.S. patent application Ser. No. 15/122,121, filed Aug. 26, 2016, which is U.S. national phase of International Application No. PCT/US2015/017950, filed Feb. 27, 2015, which designated the U.S. and claims priority to and the benefit of U.S. provisional patent application 61/945,660, filed Feb. 27, 2014 the contents of each which are incorporated herein by reference in their entirety.

TECHNICAL FIELD

The present disclosure relates generally to imaging devices and imaging devices supporting fluorescence imaging and more particularly to specular reflection detection and reduction.

BACKGROUND

In fluorescence-based imaging, a fluorescing material present in a field of view of an imaging device is excited with light of one wavelength and emits light of a different wavelength. This may provide a useful mechanism for highlighting portions of the field of view that are of particular interest to the observer. For example, in the case of fluorescence image-guided surgery, a fluorescent dye, such as indocyanine green (ICG) may be introduced to portions of a patient's anatomy to highlight those portions of the patient's anatomy. When ICG is excited with near-infrared light (approximately 750-800 nm), it fluoresces with a slightly higher wavelength (around 845 nm). By introducing ICG into selected portions of the patient's anatomy, the surgeon or other medical personnel, with the aid of a suitable viewer or camera, may receive visual cues and/or highlights that help them identify and/or avoid the selected anatomy. For example, ICG or other dyes may be used to highlight sentinel lymph nodes, areas of relative perfusion, tumor margins, and/or the like. Other useful fluorescent dyes suitable for highlighting patient anatomy include methylene blue, fluorescein, and IRDye® from LI-COR, Inc. of Lincoln, Nebraska. In some cases, the fluorescence may be in the visible band, and may not require an extra viewer or camera. While fluorescence-based imaging is being used, it is also common to use visible-light to generally illuminate other regions of the patient's anatomy about the region of interest or fluorescence so that the surgeon and/or other medical personnel may see and visualize other anatomical structures.

Unfortunately, fluorescence-based imaging is susceptible to many of the same problems as other imaging applications. Many portions of a patient's anatomy are highly reflective of light due to, for example, the presence of moisture on the surface of anatomical structures, such as tissue and/or organ structures. Because of this high reflectance, the visual light being used to generally illuminate the patient's anatomy may generate one or more areas of high specular reflection. These areas of high specular reflection may create bright spots in the images of the patient's anatomy and/or saturate the sensors used to detect the images. As a result, the areas of high specular reflection may be mistaken for fluorescing areas and/or mask or obscure the areas of fluorescence, thus limiting the usefulness of the fluorescence in detecting the selected anatomy.

Accordingly, it is desirable to provide improved methods and systems for detecting, reducing, and/or compensating for areas of high specular reflection so that a more useful fluorescence image may be obtained.

SUMMARY

Consistent with some embodiments, an imaging system includes a processing unit including one or more processors and an imaging unit coupled to the processing unit. The imaging unit includes one or more first illuminators for providing illumination of a region of interest, one or more first detectors for detecting reflections of the illumination, one or more second illuminators for triggering fluorescing of one or more fluorescent materials in the region of interest, and one or more second detectors for detecting the fluorescing of the fluorescent materials. The processing unit is configured to receive a first image from the first detectors, determine one or more regions of high specular reflection in the first image, mask out the regions of high specular reflection in the first image, and generate a composite image based on the masked first image and the detected fluorescence. The first image includes the detected reflections.

Consistent with some embodiments, a method of imaging includes emitting general illumination onto a region of interest using an imaging unit, detecting first reflections of the general illumination using the imaging unit, forming a first image based on the detected first reflections, determining one or more regions of high specular reflection in the first image, masking out the regions of high specular reflection in the first image, emitting fluorescence triggering illumination onto the region of interest using the imaging unit, detecting fluorescence of one or more fluorescent materials in the region of interest using the imaging unit, and generating a composite image based on the masked first image and the detected fluorescence.

Consistent with some embodiments, an imaging system includes a processing unit including one or more processors and an imaging unit coupled to the processing unit. The imaging unit includes one or more first illuminators providing illumination of a region of interest and one or more first detectors for detecting reflections of the illumination. The processing unit is configured to receive a first image from the first detectors, receive a second image from the first detectors, determine a first region of high specular reflection in the first image and the second image, estimate a first surface normal in the first region of high specular reflection based on differences between the first image and the second image, and provide one or more move away hints based on the estimated first surface normal. The first image includes the detected reflections and is based on a first imaging geometry. The second image includes the detected reflections and is based on a second imaging geometry different from the first imaging geometry.

Consistent with some embodiments, an imaging system includes a processing unit, an illumination system coupled to the processing unit, and a detector system coupled to the processing unit. The processing unit includes one or more processors. The illumination system emits illumination for illuminating a region of interest and triggers fluorescing of one or more fluorescent materials in the regions of interest. The detector system detects reflections of the emitted illumination and detects the fluorescing of the one or more fluorescent materials in the region of interest. The processing unit is configured to receive a first image including the detected reflections from the detector system, determine one or more regions of high specular reflection in the first image, mask out the regions of high specular reflection in the first image, and generate a composite image based on the masked first image and the detected fluorescence.

Consistent with some embodiments, a method includes accessing a masked image of a region of interest, accessing a fluorescence image of the region of interest, and generating a composite image based on the masked image and the fluorescence image. The masked image includes a first reflected image having regions of high specular reflection masked out

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
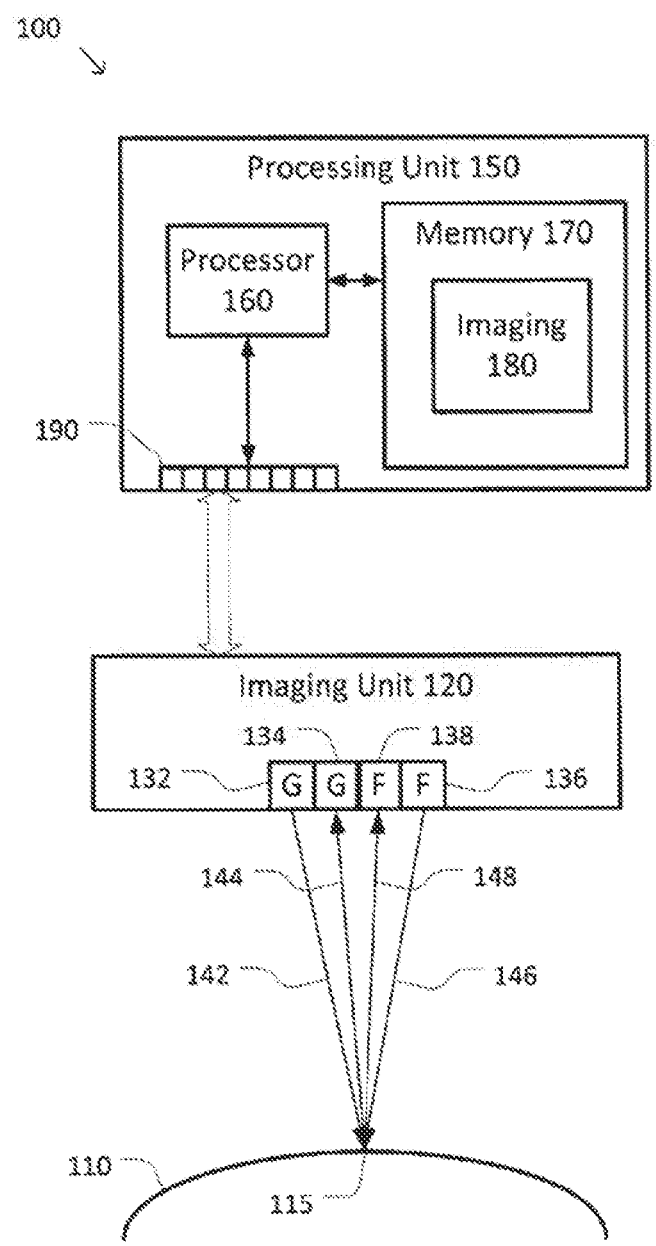
FIG. 1 is a simplified diagram of a fluorescence imaging system according to some embodiments.

FIG. 1 is a simplified diagram of a fluorescence imaging system 100 according to some embodiments. As shown in FIG. 1, a region of interest 110, such as a portion of a patient's anatomy, is shown being illuminated using an imaging unit 120. Imaging unit 120 includes several imaging emitters and detectors for illuminating the region of interest 110 and collecting one or more images of the region of interest 110 based on both the reflected illumination and fluorescence in the region of interest. Although not shown in FIG. 1, imaging unit 120 may be part of an endoscopic tool, part of an end effector on a computer-assisted surgical device that corresponds to a da Vinci® Surgical System commercialized by Intuitive Surgical, Inc. of Sunnyvale, California, and/or part of a computer-assisted imaging device. To support fluorescence imaging, imaging unit 120 may include at least two types of imaging emitters and detectors.

A general illuminator 132 is used to shine light on the region of interest 110 as shown by the example light ray 142, which reaches the region of interest 110 at an incidence point 115. When light ray 142 reaches the region of interest 110, it may be reflected off the region of interest 110 according to diffusion, reflectance, specular reflectance, and/or other imaging properties of the region of interest 110 at incidence point 115. The reflected light is modeled as an example light ray 144 that is reflected back toward imaging unit 120 where it is detected by a general illumination detector 134. Incidence point 115 may be of particular interest during imaging because imaging unit 120, and more particularly general illuminator 132 and general illumination detector 134 are located approximately near or above the surface normal at incidence point 115. When incidence point 115 has a high specular reflectance, such as due to moisture at incidence point 115, general illumination detector 134 may detect a high level of light and/or may become saturated. As a result, incidence point 115 may appear as a bright spot on images of the region of interest 110 being taken by imaging unit 120. By monitoring these images and looking for areas of high intensity and/or saturation, imaging unit 120 and/or a system such as a processing unit 150 may detect regions of likely high specular reflection within the region of interest 110.

Imaging unit 120 further includes fluorescence imaging elements. A fluorescence triggering illuminator 136 may emit one or more wavelengths of light, such as shown by the example light ray 146 that is shown reaching the region of interest 110 at incidence point 115. When light ray 146 reaches incidence point 115, fluorescent material, if present, absorbs the light and responds by fluorescing at another wavelength as shown by the representative light ray 148 that returns to imaging unit 120 where it is detected by a fluorescence detector 138. For example, when the fluorescing material is ICG, the incident light of light ray 146 and the fluorescence light of light ray 148 may be in the near infrared spectrum, but at different wavelengths.

According to some embodiments, general illuminator 132 and/or fluorescence triggering illuminator 136 may be any kind of light and/or electromagnetic emitter that may emit light at appropriate frequencies/wavelengths and/or frequency bands. In some examples, each of the illuminators may include one or more light emitting diodes, laser diodes, halogen light sources, and/or the like. According to some embodiments, general illumination detector 134 and/or fluorescence detector 138 may be any kind of detector that may detect light or electromagnetic signals at appropriate frequencies/wavelengths and/or frequency bands. In some examples, each of the detectors may include one or more photo transistors, charge coupled devices, active and/or passive filters such as a liquid crystal tunable filter (LCTF) and/or an acousto-optic tunable filter (AOTF), and/or the like.

Fluorescence imaging system 100 may further include a processing unit 150. Processing unit 150 may be part of a larger computing device and/or electronic system (not shown) that may receive inputs from user controls, process those inputs, implement one or more control algorithms based on those inputs, provide fluorescence images for display, and/or the like. Processing unit 150 includes a processor 160 coupled to memory 170. Operation of processing unit 150 is controlled by processor 160. And although processing unit 150 is shown with only one processor 160, it is understood that processor 160 may be representative of one or more central processing units, multi-core processors, microprocessors, microcontrollers, digital signal processors, field programmable gate arrays (FPGAs), application specific integrated circuits (ASICs), and/or the like in processing unit 150. Processing unit 150 may be implemented as a stand-alone subsystem and/or board added to a computing device or as a virtual machine. In some embodiments, processing unit 150 may be included as part of an operator workstation and/or operated separately from, but in coordination with the operator workstation.

Memory 170 may be used to store software executed by processing unit 150 and/or one or more data structures used during operation of processing unit 150. Memory 170 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 170 includes an imaging application 180 that may be used to support the generation and/or use of images of the region of interest 110, including images of fluorescence in the region of interest 110. Imaging application 180 may include one or more application programming interfaces (APIs) for implementing imaging methods that may include issuing one or more commands and/or requests for images from imaging unit 120 as well as receiving images from imaging unit 120. And although imaging application 180 is depicted as a software application, imaging application 180 may be implemented using hardware, software, and/or a combination of hardware and software.

To support imaging application 180, processing unit 150 additionally includes an interface 190 with one or more I/O ports. Interface 190 may be of any suitable type such as dedicated I/O lines, network connections such as Ethernet, inter-integrated circuit ($I^2C$) buses, serial peripheral interface (SPI) buses, parallel ports, analog I/O lines, and/or the like. Interface 190 may include one or more lines and/or buses for coupling processing unit 150 to imaging unit 120. In some examples, interface circuitry associated with interface 190 may include one or more bus controllers, I/O controllers, analog to digital convertors, digital to analog convertors, data acquisition systems, image acquisition systems, routers, switches, network switching devices, and/or the like.

As discussed above and further emphasized here, FIG. 1 is merely an example which should not unduly limit the scope of the claims. One of ordinary skill in the art would recognize many variations, alternatives, and modifications.

As one of ordinary skill will note, the geometries of FIG. 1 are not necessarily drawn to scale, but have been drawn to accent the important features of fluorescence imaging system 100 and imaging unit 120. For example, the relative size and/or positioning of general illuminator 132, general illumination detector 134, fluorescence triggering illuminator 136, and fluorescence detector 138 may be exaggerated to show these features at the expense of a more accurate depiction of the actual paths of light rays 142-148.

According to some embodiments, different arrangements between imaging unit 120 and processing unit 150 may be possible. In some examples, processing unit 150 may be part of imaging unit 120. In some examples, imaging unit 120 may be part of processing unit 150. In some examples, processing unit 150 may be coupled to more than one imaging unit 120. In some examples, imaging unit 120 may share imaging data with more than one processing unit.

According to some embodiments, different arrangements and configurations of general illuminator 132, general illumination detector 134, fluorescence triggering illuminator 136, and fluorescence detector 138 are possible. In some examples, more and/or fewer illuminators and/or detectors may be used. In some examples, the relative positioning among the illuminators and/or detectors may be altered. In some examples, the general illumination detector 134 and the fluorescence detector 138 may be combined into a single detector that may be used for both specular and/or fluorescence detection. In some examples, the combined detector may use time division and/or frequency division multiplexing to separate general images from fluorescence images. In some examples, the general illuminator 132 and the fluorescence triggering illuminator 136 may be combined into a single illuminator or emitter that may be used to generate both the general and/or fluorescence triggering illumination. In some examples, the combined illuminator may use time division and/or frequency division multiplexing with the aid of one or more active or passive filters to generate the desired illuminations. In some examples, the general illuminator 132 and the general illumination detector 134 may also be part of the general illumination and imaging system for the region of interest 110.

According to some embodiments, multiple combinations of general illuminators and general illumination detectors may be used. In some examples, multiple general illuminators and/or a single general illuminator may generate general light rays at multiple frequencies/wavelengths and/or frequency bands. Corresponding multiple general illumination detectors and/or a single general illumination detector may detect each of the multiple frequencies/wavelengths and/or frequency bands and generate images for each of the multiple frequencies/wavelengths and/or frequency bands. In some examples, regions of high specular reflection may be detected when high intensity and/or saturation is detected at the same locations in each of the images.

The presence of regions of high specular reflection in images may not generally be desirable. The regions of high intensity and/or saturation caused by the high specular reflections may reduce the quality and/or usefulness of the images that contain them. In some examples, the regions of high specular reflection may distract a viewer of images containing them from other important regions in the images. In some examples, the regions of high specular reflection may be mistaken for fluorescing areas and/or mask and/or cover up features in the region of interest, such as fluorescence, that may be otherwise visible, but for the presence of the high specular reflections.

Many techniques have been developed to detect, reduce, and/or compensate for regions of high specular reflection in images. One such approach is to detect regions with a high intensity that have a high likelihood of being associated with a high specular reflection and masking off those portions of the image. In some examples, this may include comparing the intensity of pixels within the image to a threshold, such as a set percentage of saturation, and replacing any pixels with intensities above the threshold with a replacement color, such as black or a color designating masking. This approach may also include identifying and/or highlighting the boundaries of the regions that are masked off. This approach may remove the distractions that the regions of high specular reflection cause, but it may also inappropriately mask off regions with high intensity not caused by high specular reflection as well as remove other important features from the image, as the masked off regions generally include no underlying image detail.

Another approach uses two sets of image sensors. When regions of high intensity, such as those caused by high specular reflection are detected in one of the images, the corresponding region from the other image is substituted. This approach reduces the likelihood of masking off desired image detail, but may require that the two sets of image sensors be sufficiently spaced apart so that high specular reflection may not occur in the same region of both images.

Other approaches may use creative shielding and/or baffles about the illuminators/emitters and image detectors to reduce the likelihood that regions of the high specular reflection may be captured by the image detectors. This approach may generally require tight control over relative positioning of the illuminators/emitters and detectors and may not generalize well to each possible geometry of the imaging unit and the region of interest.

A common approach used with fluorescence imaging is to reduce the general illumination provided by the general illuminators and use a combined visual detector for both the general illumination and the fluorescence. By reducing the general illumination, the general illumination and/or the regions of high specular reflection that may be generated are less likely to cover-up the image information obtained due to the fluorescence triggering illumination of the fluorescing material. This approach, however, tends to generate images with low levels of ambient light that may make it difficult to observe features of interest in the region of interest.

Consequently, most approaches for the detection, reduction, and/or compensation for regions of high specular reflection do not provide great solutions when images showing both visible detail and fluorescence detail are desired. This is because important visible detail is sacrificed, fluorescence detail may be masked off, and/or the solution may include equipment with geometries that are not practical for use with endoscopic and/or similar equipment. An improved solution may be obtained through use of an imaging system, such as fluorescence imaging system 100, which permits the separate collection of general illumination images from fluorescence images. In this way, the detection, reduction, and/or compensation for regions of high specular reflection may be significantly less likely to mask-out and/or cover up important fluorescence information.

Figure 2:
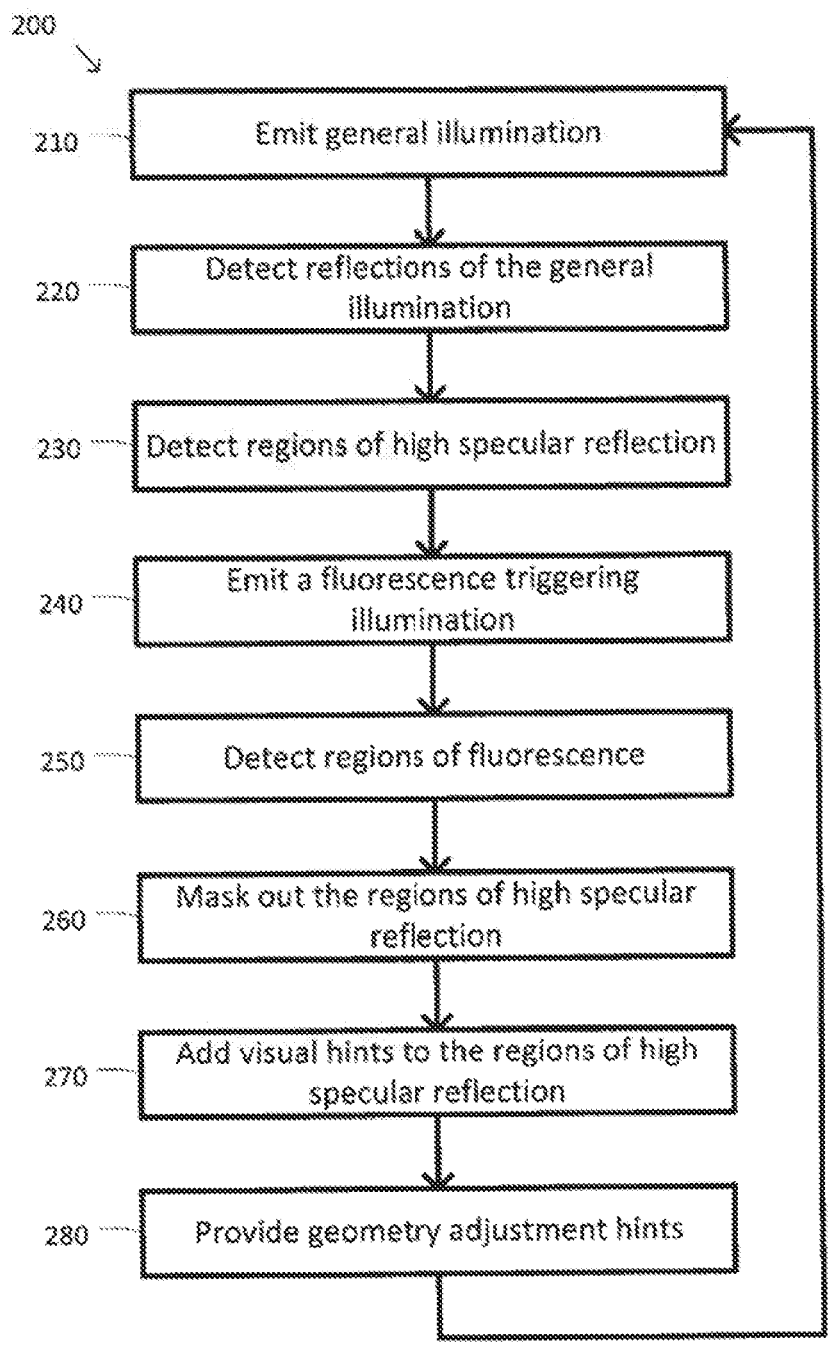
FIG. 2 is a simplified diagram of a method of high specular reflection detection and reduction according to some embodiments.

FIG. 2 is a simplified diagram of a method 200 of high specular reflection detection and reduction according to some embodiments. One or more of the processes 210-280 of method 200 may be implemented, at least in part, in the form of executable code stored on non-transient, tangible, machine readable media that when run by one or more processors, may cause the one or more processors (e.g., processor 160) to perform one or more of the processes 210-280. In some embodiments, the high specular reflection detection and reduction may be performed by an imaging application, such as imaging application 180.

At a process 210, general illumination is emitted. Using one or more general illuminators or emitters, such as general illuminator 132, general illumination is shined on a region of interest. In some examples, the general illumination may include visible light in one or more bands of the visible spectrum. In some examples, the general illuminators may be turned on using suitable driver and/or modulation circuits. In some examples, the general illuminators may each include one or more light emitting diodes, laser diodes, halogen light sources, and/or the like. In some examples, when the general illumination includes signals from multiple frequency bands, the multiple frequency bands may be emitted concurrently and/or via time division multiplexing.

At a process 220, reflections of the general illumination are detected. Using one or more general illumination detectors, such as general illumination detector 134, reflections of the general illumination emitted during process 210 are detected. In some examples, the general illumination may be reflected off of one or more structures, objects, portions of patient anatomy, and/or the like. In some examples, the one or more general illumination detectors may detect the general illumination in each of the frequency bands emitted by the general illuminators and/or a subset thereof. In some examples, each of the general illumination detectors may include one or more photo transistors, charge coupled devices, active and/or passive filters such as a LCTF and/or an AOTF, and/or the like. In some examples, the one or more general illumination detectors may be time multiplexed in synchronization with the one or more general illuminators. In some examples, the detected general illumination may be detected as a single image and/or multiple images of the region of interest with each of the multiple images corresponding to the frequency bands being emitted and/or detected for that corresponding image. In some examples, the single image and/or the multiple images may be preprocessed. In some examples, the preprocessing may include histogram equalization and/or contrast adjustment.

At a process 230, one or more regions of high specular reflection are detected. Each of the images detected during process 220 may be analyzed to determine one or more regions of potential high specular reflection. In some examples, the one or more regions of potential high specular reflection may be determined by identifying one or more regions in the images with a high intensity and/or saturation. In some examples, high intensity may be determined for any pixel with intensity above a threshold. In some examples, the threshold may be set by an operator and/or in response to other properties of the imaging system. In some examples, the threshold may be set as an absolute intensity threshold value or as a percentage of the largest possible intensity value. In some embodiments, when a single image is detected during process 220, the regions of potential high specular reflection may be the one or more regions of high specular reflection. In some embodiments, when multiple images are detected during process 220, high specular reflection may be detected in a region where each of the multiple images includes that region among the one or more regions of high potential specular reflection. In some examples, because high specular reflection is generally independent of wavelength, use of the multiple images may reduce likelihood that a region may be misclassified as a region of high specular reflection by testing for high specular reflection at multiple frequencies or in multiple frequency bands.

At a process 240, a fluorescence triggering illumination is emitted. Using one or more fluorescence triggering illuminators or emitters, such as fluorescence triggering illuminator 136, fluorescence triggering illumination is shined on a region of interest. In some examples, the fluorescence triggering illumination may include frequencies in the near infrared band. In some examples, the fluorescence triggering illuminators may be turned on using suitable driver and/or modulation circuits. In some examples, the fluorescence triggering illuminators may each include one or more light emitting diodes, laser diodes, halogen light sources, and/or the like. In some examples, when the fluorescence triggering illuminators may be the same as the general illuminators, but with modulations and/or driving circuits suitable for generating fluorescence triggering illumination rather than general illumination. In some examples, the driving circuits may include one or more active or passive filters, such as a LCTF and/or an AOTF.

At a process 250, one or more regions of fluorescence are detected. Using one or more fluorescence detectors, such as fluorescence detector 138, fluorescence of the fluorescent material in the region of interest is detected. In some examples, high specular reflection from the fluorescence illumination may not be detected during process 250 because the fluorescence detectors are generally not sensitive to the frequencies being emitted by the fluorescence triggering illuminators. In some examples, one or more of the fluorescence detectors may be the same detectors as the one or more general illumination detectors. In some examples, each of the fluorescence detectors may include one or more photo transistors, charge coupled devices, active and/or passive filters such as a LCTF and/or an AOTF, and/or the like. In some examples, the detected fluorescence may be detected as a fluorescence image. In some examples, the fluorescence image may also correspond to a general illumination image.

At a process 260, the one or more regions of high specular reflection are masked out. In some examples, the one or more regions of high specular reflection detected during process 230 may be masked out of one or more general illumination images taken of the region of interest. In some examples, the masking out may include replacing the pixels in the one or more regions with pixels of a background or default color such as black. In some examples, when the general illumination images also include fluorescence information, the fluorescence information in the regions of high specular reflection may also be masked out. In some embodiments, when the general illumination images are separate from the fluorescence image detected during process 250, the fluorescence image information may be combined with the general illumination images using an image combining algorithm such as alpha blending and/or the like. These one or more composite images may then be used for the remaining processes of method 200.

At a process 270, visual hints may be added to the regions of high specular reflection. Because the masking out of process 260 may obscure the presence of the one or more regions of high specular reflection, one or more visual hints may be added to the masked out one or more general illumination images and/or the one or more composite images to alert an operator to the potential for poorer quality and/or incomplete image information in the one or more regions of high specular reflection. In some examples, the visual hints may include adding outlines around one or more of the regions of high specular reflection, adding false color, adding patterning, adding scintillation, adding arrows and/or other markings, and/or the like.

At a process 280, one or more geometry adjustment hints are provided. Because the masking off of the one or more regions of high specular reflection during process 260 may remove and/or degrade information in the one or more general illumination images and/or composite images, geometry adjustment hints may be provided to an operator and/or a motion planning system for the imaging unit. By adjusting the geometry of the imaging unit it may be possible to reduce the size of and/or remove one or more of the regions of high specular reflection in the one or more general illumination images and/or composite images because the orientation of the imaging relative to the surface normals in the region of interest may change. In some examples, the geometry adjustment hints may include audio hints, visual cues, such as arrows, in the one or more general illumination images and/or composite images, feedback applied to operator input controls, feedback applied to motion planning algorithms, and/or the like.

Method 200 may further include repeating processes 210-280 to remove regions of high specular reflection in multiple images and/or to generate a video image of the region of interest.

As discussed above and further emphasized here, FIG. 2 is merely an example which should not unduly limit the scope of the claims. One of ordinary skill in the art would recognize many variations, alternatives, and modifications. In some embodiments, method 200 may be modified to take advantage of the ability to move the imaging unit relative to the region of interest using motion planning algorithms. In some examples, an operator or other system using the imaging application may specify a volume in which the imaging unit may be moved without interfering with other devices, objects, and/or patient anatomy in or near the region of interest. The imaging application may then move the imaging unit about the volume collecting a sequence of general illumination, and/or fluorescence images. Regions of high specular reflection in some of the images may be replaced with images of the same regions from other images that have reduced or no specular reflection. In some examples, one or more image stitching algorithms may be used to create a composite image with the reduced and/or eliminated specular reflection. In some examples, one or more kinematic models of the imaging unit and the device moving the imaging unit through the volume may be used to cross correlate the regions from different images. In some examples, when the region of interest includes moving objects and/or moving patient anatomy (e.g., a beating heart), the image collection may be timed so that the sequence of images correspond to roughly the same positions, phases, and/or orientations of objects and/or patient anatomy in the region of interest.

Figure 3:
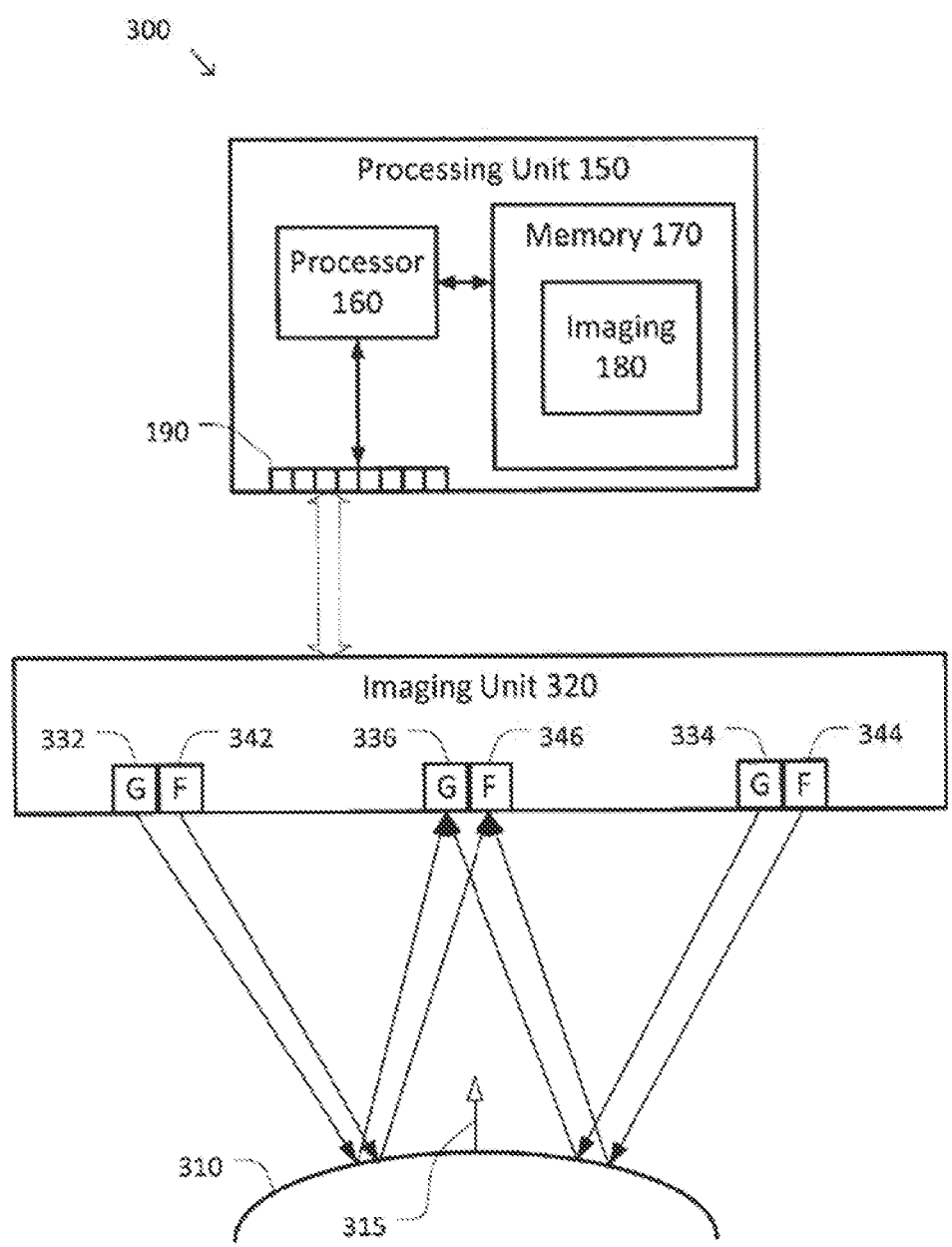
FIG. 3 is a simplified diagram of another fluorescence imaging system according to some embodiments.

FIG. 3 is a simplified diagram of another fluorescence imaging system 300 according to some embodiments. As shown in FIG. 3, a region of interest 310, such as a portion of a patient's anatomy, is shown being illuminated using an imaging unit 320. Imaging unit 320 includes several imaging emitters and detectors for illuminating the region of interest 310 and collecting one or more images of the region of interest 310 based on both the reflected illumination and fluorescence in the region of interest. Although not shown in FIG. 3, imaging unit 320 may be part of an endoscopic tool, part of an end effector on a computer-assisted surgical device, and/or part of a computer-assisted imaging device. To support fluorescence imaging, imaging unit 320 may include several sets and types of imaging emitters and detectors.

Imaging unit 320 includes at least two general illuminators 332 and 334 spaced at a known distance apart. In some examples, each of the general illuminators 332 and 334 may be similar to general illuminator 132. Each of the general illuminators 332 and 334 is configured to shine general illumination on the region of interest 310 as shown by the respective example light ray arrows from general illuminators 332 and 334 to the surface in the region of interest. The general illumination is reflected off the surface in the region of interest based on the geometry of the surface as approximated by a surface normal 315 near the corresponding points where the general illumination is incident on the surface of the region of interest 310. The reflected general illumination is returned to imaging unit 320 where it may be captured in separate stereoscopic images by a general illumination detector 336. In some examples, general illumination detector 336 may be similar to general illumination detector 134. In some examples, general illuminators 332 and 334 may alternate providing illumination on the region of interest 310 so that the separate stereoscopic images may be captured using the illumination from one of the general illuminators 332 and 334 at a time. Using the separate stereoscopic images and the known geometries of the general illuminators 332 and 334 and the general illumination detector 336, imaging unit 320 and/or a processing unit coupled to imaging unit 320 such as processing unit 150 may determine an approximate location and/or orientation of surface normal 315 as well as other surface normals that may be located at other locations in region of interest 310. In some examples, the separate stereoscopic images may also be used to detect one or more regions of high specular reflection in region of interest 310.

Similar to imaging unit 120, imaging unit 320 may also include fluorescence triggering illuminators 342 and 344 as well as a fluorescence detector 346. In some examples, each of fluorescence triggering illuminators 342 and 344 may be similar to fluorescence triggering illuminator 136 and fluorescence detector 346 may be similar to fluorescence detector 138. Either or both of fluorescence trigger illuminators 342 and 344 may be used to trigger fluorescence of fluorescent material in region of interest 310. Fluorescence detector 346 may detect the fluorescence triggered by fluorescence triggering illuminators 342 and 344.

By approximating surface normals like surface normal 315, imaging unit 320 is better able to provide geometry adjustment hints as described with respect to process 280. The position and orientation of a surface normal may be used to provide better move away hints for imaging unit 320 because the orientation with highest specular reflection typically occurs when both the general illuminators and the general illumination detector are positioned above and oriented toward the surface normal. Thus, avoiding orientations where imaging unit 320 is directly or approximately in alignment with a surface normal like surface normal 315 may reduce and/or eliminate high specular reflection caused by the surface at those surface normals.

As discussed above and further emphasized here, FIG. 3 is merely an example which should not unduly limit the scope of the claims. One of ordinary skill in the art would recognize many variations, alternatives, and modifications.

As one of ordinary skill will note, the geometries of FIG. 3 are not necessarily drawn to scale, but have been drawn to accent the important features of fluorescence imaging system 300 and imaging unit 320. For example, the relative size and/or positioning of the illuminators and detectors may be exaggerated to show these features at the expense of a more accurate depiction of the actual paths of the corresponding light rays in FIG. 3.

According to some embodiments, different arrangements between imaging unit 320 and processing unit 150 may be possible. In some examples, processing unit 150 may be part of imaging unit 320. In some examples, imaging unit 320 may be part of processing unit 150. In some examples, processing unit 150 may be coupled to more than one imaging unit 320. In some examples, imaging unit 320 may share imaging data with more than one processing unit.

According to some embodiments, different arrangements and configurations of the illuminators and detectors may also provide the desired stereoscopic images, detection of the regions of high specular reflection, and detection of the fluorescence images. In some examples, more and/or fewer illuminators and/or detectors are possible. In some examples, the two general illuminators 332 and 334 and general illumination detector 336 may be replaced with two general illumination detectors with a known spacing and one general illuminator. In some examples, one or the other of fluorescence triggering illuminators 342 and/or 344 may be omitted. In some examples, the remaining fluorescence triggering illuminator may be moved into closer proximity with fluorescence detector 346. In some examples, time division and/or frequency division multiplexing may be used to combine the general illuminators and the fluorescence triggering illuminators (e.g., general illuminator 332 and fluorescence triggering illuminator 342). In some examples, time division and/or frequency division multiplexing may be used to combine general illumination detector 336 and fluorescence detector 346.

Figure 4:
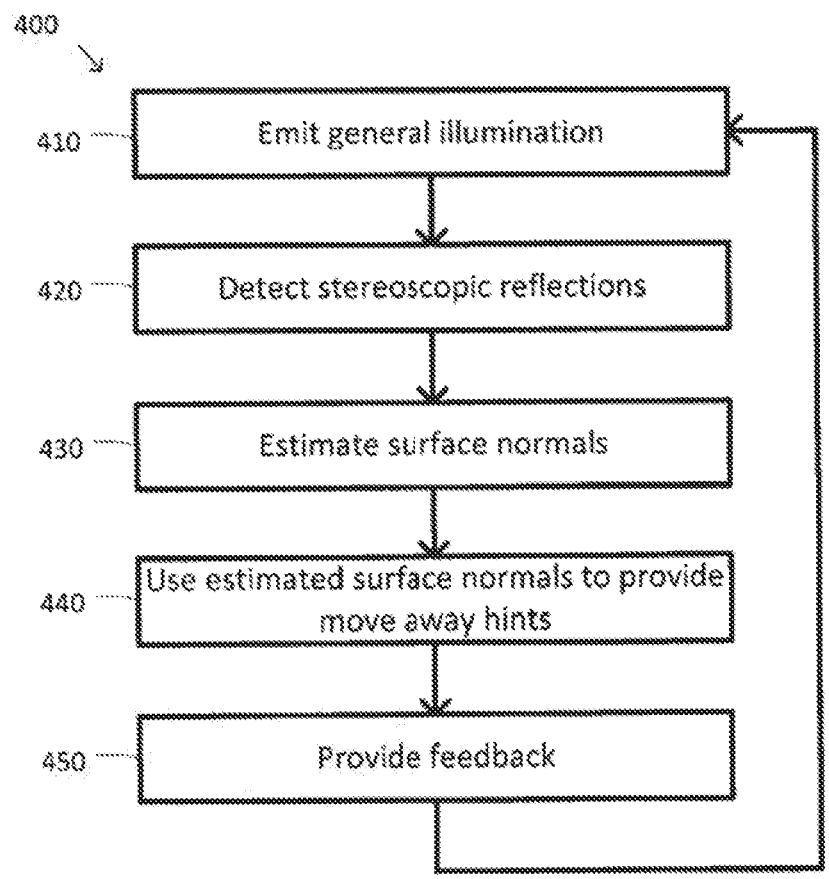
FIG. 4 is a simplified diagram of another method of high specular reflection detection and reduction according to some embodiments.

FIG. 4 is a simplified diagram of another method 400 of high specular reflection detection and reduction according to some embodiments. One or more of the processes 410-450 of method 400 may be implemented, at least in part, in the form of executable code stored on non-transient, tangible, machine readable media that when run by one or more processors, may cause the one or more processors (e.g., processor 160) to perform one or more of the processes 410-450. In some embodiments, the high specular reflection detection and reduction may be performed by an imaging application, such as imaging application 180. In some embodiments, method 400 may be performed in conjunction with method 200 to provide both masking of one or more regions of high specular reflection and to provide move away hints to reduce the amount of high specular reflection captured by an imaging system.

At a process 410, general illumination is emitted. Using one or more general illuminators or emitters, such as general illuminators 332 and/or 334, general illumination and/or general illumination is shined on a region of interest. In some examples, the general illumination may include visible light in one or more bands of the visible spectrum. In some examples, the general illuminators may be turned on using suitable driver and/or modulation circuits. In some examples, the general illuminators may each include one or more light emitting diodes, laser diodes, halogen light sources, and/or the like. In some examples, when the general illumination includes signals from multiple frequency bands, the multiple frequency bands may be emitted concurrently and/or via time division multiplexing.

At a process 420, stereoscopic reflections are detected. Using one or more general illumination detectors, such as general illumination detector 336, in conjunction with the one or more general illuminators, two or more stereoscopic images of the reflected general illumination are obtained. In some examples, the general illumination may be reflected off of one or more structures, objects, portions of patient anatomy, and/or the like. In some examples, the one or more general illumination detectors may detect the general illumination in each of the frequency bands emitted by the one or more general illuminators and/or a subset thereof. In some examples, each of the general illumination detectors may include one or more photo transistors, charge coupled devices, active and/or passive filters such as a LCTF and/or an AOTF, and/or the like. In some examples, the one or more general illumination detectors may be time multiplexed in synchronization with the one or more general illuminators.

At a process 430, surface normals are estimated. The stereoscopic images detected during process 420 may be used to estimate the surface normals for one or more surfaces visible in the stereoscopic images. In some examples, the known differences in the imaging geometry between the two stereoscopic images may be used to estimate the surface normals based on the differences in the stereoscopic images. In some examples, stereoscopic camera calibration data may be used to estimate the surface normals. In some examples, the surface normals may be estimated for the one or more surfaces at numerous locations on those surfaces. In some examples, a process similar to process 230 may be used to detect regions of high or potentially high specular reflection with the surface normals being estimated within those detected regions.

At a process 440, the estimated surface normals are used to provide move away hints. The one or more estimated surface normals point to locations above the one or more surfaces in the region of interest that the imaging unit should avoid approaching to reduce and/or eliminate the amount of high specular reflection in detected and/or captured images. To discourage positioning of the imaging unit above the one or more surface normals and/or to encourage movement of the image unit away from alignment with the one or more surface normals, move away hints may be provided to an operator and/or a motion planning system for the imaging unit. In some examples, the move away hints may be provided based on one or more kinematic models of the device arm on which the imaging unit is mounted.

In some embodiments, the one or more move away hints may include adding visual hints, such as arrows, in the images displayed to operators that suggest a direction of movement and/or a change in orientation for the imaging unit. In some examples, the direction of movement may be away from locations pointed to by the one or more surface normals. In some examples, when the imaging unit is positioned near one of the locations pointed to by one of the surface normals, the movement hint may include a limited set of directions away from the surface normal. In some examples, when the imaging unit is aligned with the surface normal, the movement hint may suggest any direction away from the surface normal. In some examples, when the surface normal may be avoided by a change in position and/or orientation, the movement hint may suggest an appropriate rotation of the imaging unit away from the surface normal. In some examples, the rotation may be determined based on one or more kinematic models of the device arm on which the imaging unit is mounted.

In some embodiments, the one or more move away hints may include audio hints. In some examples, the audio hints may include directions such as left, right, up, down, away, rotate, and/or the like. In some examples, when multi-directional sound is available, the move away hints may provide sounds that may cue an operator to move toward or away from the sound. In some examples, the sound intensity may increase or decrease as the audio hints are being successfully followed.

In some embodiments, the one or more move away hints may include adding one or more move away points and/or lines in a motion planning geometry. In some examples, the one or more move away points and/or lines may be implemented using one or more points or areas with repulsing fields and/or repulsing charges. In some examples, the one or more move away points and/or lines may be implemented using one or more virtual collision objects and/or virtual feedback mechanisms. In some examples, the one or more move away points may be pointed to by a respective surface normal and located at a height above the respective surface normal based on a working distance of the imaging unit. In some examples, the one or more move away points may be pointed to by a respective surface normal and located near a current position of the imaging unit. In some examples, the one or more move away lines may be collinear with the surface normal and extend from the surface through at least a height of the imaging unit.

At a process 450, feedback is provided. In some embodiments, the one or more move away points and/or lines may be used to alter a motion plan for the imaging unit. In some examples, the one or more move away points and/or lines may create repulsing forces and/or torques that may induce feedback forces and/or torques on the joints of the imaging unit. In some examples, the induced feedback forces or torques may modify the forces or torques for the corresponding joints for the imaging unit determined from other motion planning and/or operator commanded movements. In some examples, a Jacobian transpose or similar method may be used to map the repulsing forces and/or torques to the induced feedback forces and/or torques. In some examples, the feedback forces and/or torques may also be fed back to the operator through one or more haptic control devices.

Method 400 may further include repeating processes 410-450 to periodically estimate surface normals and provide move away hints and feedback to operators and/or motion planning systems.

As discussed above and further emphasized here, FIG. 4 is merely an example which should not unduly limit the scope of the claims. One of ordinary skill in the art would recognize many variations, alternatives, and modifications. In some embodiments, method 400 may be modified to take advantage of the ability to move the imaging unit relative to the region of interest using motion planning algorithms. In some examples, an operator or other system using the imaging application may specify a volume in which the imaging unit may be moved without interfering with other devices, objects, and/or patient anatomy in or near the region of interest. The imaging application may then move the imaging unit about the volume collecting a sequence of stereoscopic images. In some examples, the collection of stereoscopic images may be analyzed to determine one or more poses for the imaging unit that most reduces positioning and/or alignment of the imaging unit with each of the surface normals in the region of interest. In some examples, the collection of stereoscopic images may be analyzed to predict preferred poses for the imaging unit to avoid high specular reflection for selected regions within the region of interest and/or to determine a group of preferred poses for use by method 200 to stitch together a composite image with reduced and/or eliminated specular reflection. In some examples, when the region of interest includes moving objects and/or moving patient anatomy (e.g., a beating heart), the image collection may be timed so that the sequence of stereoscopic images correspond to roughly the same positions, phases, and/or orientations of objects and/or patient anatomy in the region of interest.

Some examples of processing units, such as processing unit 150 may include non-transient, tangible, machine readable media that include executable code that when run by one or more processors (e.g., processor 160) may cause the one or more processors to perform the processes of methods 200 and/or 400. Some common forms of machine readable media that may include the processes of methods 200 and/or 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An imaging system comprising:
a processing unit comprising one or more processors; and
an imaging unit coupled to the processing unit and comprising:
one or more first illuminators providing illumination of a region of interest; and
one or more first detectors for detecting reflections of the illumination;
wherein the processing unit is configured to:
receive a first image from the one or more first detectors, the first image including the detected reflections and being based on a first imaging geometry;
receive a second image from the one or more first detectors, the second image including the detected reflections and being based on a second imaging geometry different from the first imaging geometry;
determine a first region of high specular reflection in the first image and the second image;
estimate a first surface normal in the first region of high specular reflection based on differences between the first imaging geometry and the second imaging geometry; and
provide a move away hint based on the estimated first surface normal, the move away hint indicating a direction of movement of the imaging unit to reduce specular reflection.

2. The imaging system of claim 1, wherein providing the move away hint comprises providing a move away line to a motion planning system, the move away line being collinear with the first surface normal.

3. The imaging system of claim 1, wherein the processing unit is further configured to:
move the imaging unit from a first pose to a second pose, the move altering the first imaging geometry to a third imaging geometry and altering the second imaging geometry to a fourth imaging geometry;
receive a third image from the one or more first detectors, the third image including the detected reflections and being based on the third imaging geometry;
receive a fourth image from the one or more first detectors, the fourth image including the detected reflections and being based on the fourth imaging geometry;
determine a second region of high specular reflection in the third image and the fourth image;
estimate a second surface normal in the second region of high specular reflection based on differences between the third imaging geometry and the fourth imaging geometry; and
select for use either the first and second images or the third and fourth images based on the first and second surface normals, the first and second regions of high specular reflection, and the first and second poses.

4. The imaging system of claim 1, wherein:
the imaging unit further comprises:
one or more second illuminators for triggering fluorescing of one or more fluorescent materials in the region of interest; and
one or more second detectors for detecting the fluorescing of the fluorescent materials; and
the processing unit is further configured to:
mask out the first region of high specular reflection in the first image to create a masked first image;
generate a fluorescence image of the region of interest; and
generate a composite image based on the masked first image and the fluorescence image.

5. The imaging system of claim 1, wherein the move away hint is based on one or more kinematic models of an arm supporting the imaging unit.

6. The imaging system of claim 1, wherein the move away hint comprises a visual hint displayed to an operator indicating a suggested direction of movement of the imaging unit.

7. The imaging system of claim 1, wherein the move away hint comprises a visual hint displayed to an operator indicating a suggested change in orientation of the imaging unit.

8. The imaging system of claim 1, wherein providing the move away hint comprises providing a move away point to a motion planning system, the move away point being pointed to by the first surface normal.

9. The imaging system of claim 8, wherein the move away point is located at a height above the first surface normal based on a working distance of the imaging unit.

10. The imaging system of claim 8, wherein the move away point is located near the imaging unit.

11. A method comprising:
receiving a first image from one or more first detectors of an imaging unit configured to detect reflections of illumination of a region of interest provided by one or more first illuminators of the imaging unit, the first image including the detected reflections and being based on a first imaging geometry;
receiving a second image from the one or more first detectors, the second image including the detected reflections and being based on a second imaging geometry different from the first imaging geometry;
determining a first region of high specular reflection in the first image and the second image;
estimating a first surface normal in the first region of high specular reflection based on differences between the first imaging geometry and the second imaging geometry; and
providing a move away hint based on the first surface normal, the move away hint indicating a direction of movement of the imaging unit to reduce specular reflection.

12. The method of claim 11, wherein providing the move away hint comprises providing a move away line to a motion planning system, the move away line being collinear with the first surface normal.

13. The method of claim 11, further comprising:
moving the imaging unit from a first pose to a second pose, the move altering the first imaging geometry to a third imaging geometry and altering the second imaging geometry to a fourth imaging geometry;
receiving a third image from the one or more first detectors, the third image including the detected reflections and being based on the third imaging geometry;
receiving a fourth image from the one or more first detectors, the fourth image including the detected reflections and being based on the fourth imaging geometry;
determining a second region of high specular reflection in the third image and the fourth image;
estimating a second surface normal in the second region of high specular reflection based on differences between the third imaging geometry and the fourth imaging geometry; and
selecting for use either the first and second images or the third and fourth images based on the first and second surface normals, the first and second regions of high specular reflection, and the first and second poses.

14. The method of claim 11, wherein the move away hint is based on one or more kinematic models of an arm supporting the imaging unit.

15. The method of claim 11, wherein the move away hint comprises a visual hint displayed to an operator indicating a suggested direction of movement of the imaging unit.

16. The method of claim 11, wherein the move away hint comprises a visual hint displayed to an operator indicating a suggested change in orientation of the imaging unit.

17. The method of claim 11, wherein providing the move away hint comprises providing a move away point to a motion planning system, the move away point being pointed to by the first surface normal.

18. The method of claim 17, wherein the move away point is located at a height above the first surface normal based on a working distance of the imaging unit.

19. The method of claim 17, wherein the move away point is located near the imaging unit.

20. A non-transitory computer-readable medium comprising a plurality of computer-readable instructions which, when executed by one or more processors, are adapted to cause the one or more processors to:
receive a first image from one or more first detectors of an imaging unit configured to detect reflections of illumination of a region of interest provided by one or more first illuminators of the imaging unit, the first image including the detected reflections and being based on a first imaging geometry;
receive a second image from the one or more first detectors, the second image including the detected reflections and being based on a second imaging geometry different from the first imaging geometry;
determine a first region of high specular reflection in the first image and the second image;
estimate a first surface normal in the first region of high specular reflection based on differences between the first imaging geometry and the second imaging geometry; and
provide a move away hint based on the first surface normal, the move away hint indicating a direction of movement of the imaging unit to reduce specular reflection.

* * * * *